US005196451A

United States Patent [19]

Greig-Smith et al.

[11] Patent Number: 5,196,451

[45] Date of Patent: Mar. 23, 1993

[54] AVIAN CONTROL

[75] Inventors: Peter W. Greig-Smith, Headley; Michael F. Wilson, Esher, both of England

[73] Assignee: National Research Development Corporation, London, England

[21] Appl. No.: 793,292

[22] Filed: Nov. 14, 1991

Related U.S. Application Data

[63] Continuation of Ser. No. 391,522, Jul. 21, 1989, abandoned.

[30] Foreign Application Priority Data

Dec. 14, 1987 [GB] United Kingdom ................. 8729109

[51] Int. Cl.$^5$ ............................................ A01N 37/10

[52] U.S. Cl. ................................... 514/570; 514/617; 514/622; 514/532

[58] Field of Search ............... 514/532, 570, 614, 699, 514/701, 617, 622

[56] References Cited

U.S. PATENT DOCUMENTS

| | | | |
|---|---|---|---|
| 2,390,249 | 2/1945 | Hall et al. | 167/30 |
| 2,933,429 | 4/1960 | Wicker et al. | 167/46 |
| 2,967,128 | 1/1961 | Kare | 167/46 |
| 3,268,408 | 8/1966 | Naito | 167/65 |
| 3,835,128 | 9/1974 | Bracha et al. | 260/240 J |
| 4,097,607 | 6/1978 | Larson | 424/324 |
| 4,153,705 | 5/1979 | Puttner et al. | 424/270 |
| 4,659,857 | 4/1987 | Kuhn | 558/58 |
| 4,767,782 | 8/1988 | Seppelt et al. | 514/543 |
| 4,775,693 | 2/1988 | Kuhn | 514/522 |

FOREIGN PATENT DOCUMENTS

| | | |
|---|---|---|
| 954286 | 12/1956 | Fed. Rep. of Germany . |
| 2529755 | 1/1984 | France . |
| 53-1818 | 1/1978 | Japan . |
| 56-52884 | 12/1981 | Japan . |
| 57-46915 | 3/1982 | Japan . |
| 595766 | 2/1978 | Switzerland . |
| 1104995 | 3/1965 | United Kingdom . |
| 1108308 | 1/1966 | United Kingdom . |

OTHER PUBLICATIONS

Mikasa Chemical CA 95: 75495k 1979.
Kokai Tokkyo Koho CA 97: 44321n 1982.
Schafer et al. CA 99: 65537u 1983.
Jung et al "Effects of Phenolic Monomers . . . " Journal of Nutrition, 1983, 113, 546–556.
Glick "Modes of Action of Gallic Acid in Suppressing . . . " Journal of Nutrition, 1981, III, pp. 1910–1916.
Kratzer et al "Characterization and Growth Depressing . . . " Poultry Science. 1975, 54, 2124–2127.
Greig-Smith "Aversions of Starlings . . . " Ethology, 74 (1987) pp. 155-163 Greig-Smith "Deter Birds—the tasteful way" New Scientist, 21 Nov. 1985; pp. 38–40.
Wilson, "Chemical Bird Deterrants . . . " Annual Meeting 1-5 Sep. 1986 British Association for the Advancement of Science, pp. 1-10.
Grazio et al "Protecting Ripening . . . " Jour. of Wildlife (List continued on next page.)

*Primary Examiner*—Frederick E. Waddell
*Assistant Examiner*—Russell Travers
*Attorney, Agent, or Firm*—Nixon & Vanderhye

[57] ABSTRACT

Compounds of formula (I), wherein $X^1$ and $X^5$ are each separately selected from hydrogen and $C_{1-4}$ alkyl, halogeno and halogeno-substituted $C_{1-4}$ alkyl groups: $X^2$, $X^3$ and $X^4$ are each separately selected from hydrogen and $C_{1-4}$ alkyl, hydroxy, $C_{1-4}$ alkoxy and phenoxy groups; $R^1$ and $R^2$ are each separately selected from hydrogen and $C_{1-4}$ alkyl groups; $R^3$ and $R^4$ are each hydrogen or together constitute the second bond of a carbon-carbon double bond joining $—CR^1R^3$ and $—CR^2R^4$; and Y is hydroxymethyl, formyl, cyano, carbamoyl, carbamoyl N-substituted by one or two of the same or different $C_{1-4}$ alkyl groups, carboxy or a carboxylic ester or carboxylate salt, are of value as avian repellents.

20 Claims, 3 Drawing Sheets

OTHER PUBLICATIONS

Management, vol. 36, No. 4, Oct. 1972, pp. 1316–1320.

Schafer, Jr. et al "Repellancy and Toxicity . . . " J. Environ. Sci. Health, A1B(4), 493–503 (1983).

Baruffini et al "Phytotoxic Activity . . . " II Farmaco -Ed. Sci. vol. XXII N. 8, pp. 612–625.

Horsfall, "Principles of Fungicidal Action", pp. 193–194.

Jones et al "Some Allelochemicals . . . " Biochem. Sys. & Eco. vol. 17, pp. 187–192.

WPIL File Supplier, AN=87-032872 [05], Derwent Publications Ltd., London, GB; & JP-A-61 289 003 (Mikasa Kagaku Kogyo) Dec. 19, 1986.

Linhart et al, "Test Methods for Determining the Efficacy of Coyote . . . " Vertebrate Pest Control, pp. 114–122.

E. W. Schafer, Jr. et al "The Acute Oral Toxicity, Repellancy . . . " Arch. Environm. Contam. Toxicol., 12, 355–382 (1983).

E. W. Schafer, Jr. "Repellency and Toxicity of 55 Insect . . ." J. Environ. Sci. Health, A18(4), 493–502 (1983).

E. W. Schafer, Jr. et al "Chemicals as Bird Repellents . . . " Journal of Wildlife Management, vol. 35, No. 3 Jul. 1971, pp. 569–572.

Starr et al "A Laboratory Method for Evaluating . . . " Agricultural & Food Chemistry, vol. 12, No. 4, Jul.-Aug. 1964, pp. 342–344.

AVIAN CONTROL

This is a continuation of application Ser. No. 07/391,522, filed Jul. 21, 1989, now abandoned.

This invention relates to the control of birds and in particular to compounds of use as avian repellents.

The protection of agricultural and horticultural crops from damage by pest birds is of considerable importance but there are very few means of adequately controlling birds in such situations without resorting to physical barriers or ineffective, inhumane or environmentally unacceptable chemicals. Attempts have therefore been made to identify compounds occurring naturally in fruit buds which act as avian deterrents, many of which are phenolics of quite complex structure and/or high molecular weight whose action has often been attributed to the ability of tannins to precipitate proteins thereby conferring astringency on foods. However these attempts have not produced a suitable compound for use in the field.

The present invention has developed from an investigation of a group of relatively simple synthetic compounds, some of which contain phenolic groups and many of which do not, and which as far as we are aware have never been identified as occurring in fruit buds. This investigation has led to the discovery of a range of compounds which exhibit varying levels of avian repellent activity.

Accordingly, the present invention comprises the use as an avian repellent of a compound of formula (I)

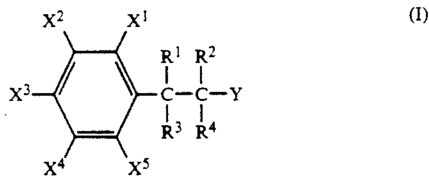

wherein $X^1$ and $X^5$ are each separately selected from hydrogen and $C_{1-4}$ alkyl, halogeno and halogeno-substituted $C_{1-4}$ alkyl groups; $X^2$, $X^3$ and $X^4$ are each separately selected from hydrogen and $C_{1-4}$ alkyl, hydroxy, $C_{1-4}$ alkoxy and phenoxy groups; $R^1$ and $R^2$ are each separately selected from hydrogen and $C_{1-4}$ alkyl groups; $R^3$ and $R^4$ are each hydrogen or together constitute the scond bond of a carbon—carbon double bond joining $—CR^1R^3—$and $—CR^2R^4—$; and Y is hydroxymethyl, formyl, cyano, carbamoyl, carbamoyl N-substituted by one or two of the same or different $C_{1-4}$ alkyl groups, carboxy or a carboxylic ester or carboxylate salt.

The compounds (I) may exist in various stereoisomeric forms but in the case of the compounds in which $R^3$ and $R^4$ represent the second bond of a carbon—carbon double bond, i.e. cinnamic acid and its derivatives and analogues, the preference is for the commonly occurring trans isomeric form rather than the cis isomeric form.

General preferences among the compounds of formula (I) are as follows. $X^1$ and $X^5$ are conveniently each separately selected from hydrogen or to a lesser extent from $C_{1-4}$ alkyl, or alternatively from a halogeno group such as fluoro, chloro, bromo or iodo, or to a lesser extent additionally from a halogeno-substituted methyl group, for example trifluoromethyl. $X^2$, $X^3$ and $X^4$ are conveniently each separately selected from hydrogen and $C_{1-4}$ alkoxy groups, especially ethoxy and particularly methoxy, or to a lesser extent additionally from phenoxy and also hydroxy. As regards $R^1$ and $R^2$ these are preferably each separately selected from hydrogen, methyl and ethyl, especially from methyl and particularly from hydrogen. Conveniently each of $R^1$ and $R^2$ is hydrogen or one is hydrogen, preferably $R^2$, and the other is a $C_{1-4}$ alkyl group, preferably methyl. $R^3$ and $R^4$ preferably together constitute the second bond of a double bond. In the case of Y this is preferably a formyl group or more especially a carboxy group or an ester or salt thereof, and particularly a carbamoyl group substituted by two or especially one $C_{1-4}$ alkyl group, for example ethyl or particularly methyl, or especially an unsubstituted carbamoyl group. Esters may conveniently be formed with aliphatic or aromatic alcohols, particularly those containing a $C_1$–$C_{24}$ aliphatic hydrocarbon group, for example an alkyl or alkenyl group, or an aromatic hydrocarbon group such as an unsubstituted or substituted napthyl or particularly phenyl group, whilst salts may be formed with various organic or inorganic bases, for example an alkali metal hydroxide such as sodium hydroxide, a quaternary ammonium hydroxide or an amine such as 2-amino-2-hydroxymethyl propane 1,3-diol (tris). The use of such derivatives, which are conveniently of physiologically acceptable form, may be of value in formulation. Thus esters containing the larger aliphatic hydrocarbon groups will be less water soluble than the free acid and many salts will be more water soluble.

Compounds of some particular interest have $X^2$ and $X^4$ which are each separately a $C_{1-4}$ alkoxy group, for example an ethoxy or especially a methoxy group, conveniently together with groups $X^1$, $X^3$ and $X^5$ in which $X^1$ and $X^5$ are each hydrogen and $X^3$ is $C_{1-4}$ alkoxy, for example ethoxy or especially methoxy or preferably which are each hydrogen. Alternatively, other compounds of particular interest have $X^1$, $X^2$, $X^3$, $X^4$ and $X^5$ which are each hydrogen. Such compounds of particular interest may conveniently have $R^3$ and $R^4$ which constitute a second bond of a carbon—carbon double bond, particularly together with $R^1$ and $R^2$ which are each hydrogen; Y especially being either carboxy or to a lesser extent a carboxylic ester or carboxylate salt, or more preferably a carbamoyl group or to a lesser extent an N-substituted carbamoyl group.

Examples of specific compounds of use in the present invention are (1) 3,5-dimethoxycinnamic acid and its salts and esters;
(2) 3,4,5-trimethoxycinnamic acid and its salts and esters;
(3) 3,5-dimethoxycinnamamide;
(4) 3,4,5-trimethoxycinnamamide; and
(5) cinnamamide.

Of these compounds (1), (3) and (5) are of most interest with (1) and especially (5) being preferred for use as an avian repellent.

The present invention relating to the use of the compounds of formula (I) as avian repellents is not limited by any theory as to the mode of action of the repellents. However, since we believed that the particular effectiveness of the compounds of formula (I) as avian repellents might lie in their ability to inhibit the biochemical process of enzymatic proteolysis which takes place in the small intestine of the bird we have investigated such inhibition. This inhibition reduces the nutritional quality of foodstuffs ingested by the bird and in turn discourages it from further feeding on a treated crop. Our experiments have shown that many of the compounds of formula (I) affect the alkaline serine protease activity in the small intestine of the bird to some degree and we have been able to show that the inhibition of enzyme activity is caused by the compounds (I) selectively and non-competitively binding at or about the active site of the alkaline serine protease and thereby reducing the potential of this site for binding and hydrolysing its normal, protein substrate.

The major alkaline serine protease in birds is either chymotrypsin, for example in the quail and starling, or trypsin, for example in the bullfinch and pigeon. It has been found that the relative degree of inhibition of chymotrypsin and trypsin varies between the various compounds (I). If the avian repellent activity of the compounds (I) were based primarily on their enzyme inhibiting ability this finding would have potentially important consequences since to optimize the repellent effect on all birds the use would be indicated of either a compound (I) which is effective against both chymotrypsin and trypsin or of a mixture of compounds (I), one of which is particularly effective against chymotrypsin and another against trypsin. Alternatively, it may be desirable in certain situations to repel some birds but not others. Thus, for example, bullfinches are particularly destructive of fruit buds but most other birds cause less damage and can have a beneficial effect through the control they exert upon the insect population. This raises the possibility that it could be advantageous to repel bullfinches selectively, a possible approach being the use of a compound (I) showing a high degree of inhibition of trypsin but a low level of inhibition of chymotrypsin.

Preferences among the compounds (I) will therefore now be discussed further with particular reference to our findings on their inhibitory effect upon the two enzymes chymotrypsin and trypsin. However, it will be appreciated that the compounds (I) will exert an effect at two levels, a first effect which depends simply on their distasteful nature and a second effect which depends on their effect on the bird's digestion. Although the second effect is likely to be species dependent the first is not. Indeed, as will be discussed in more detail hereinafter, in feeding trials the first effect appeared to be the predominant one since the degree of reluctance to consume food treated with a compound (I) did not correlate closely with the enzyme inhibiting activity of the compound (I).

As regards activity against trypsin, compounds (I) in which $X^1=X^2=X^3=X^4=X^5=H$ and $Y=CONH_2$ (or a substituted carbamoyl group) or $CO_2H$ (or an ester or salt derivative thereof), conveniently with $R^1=R^2=H$ and $R^3+R^4$=bond, generally tend to be especially effective inhibitors of trypsin. The $Y=CO_2H$ compound was observed to be somewhat more active than the equivalent $Y=CONH_2$ compound and, indeed, when tested against pigeon intestinal trypsin rather than bullfinch intestinal trypsin no activity was observed for cinnamamide. By contrast with the inhibition of chymotrypsin, as discussed hereinafter, compounds (I) in which $X^1$ and $X^5$ are hydrogen and one or more of $X^2$, $X^3$ and $X^4$ is a hydroxy or alkoxy group, for example a methoxy group, generally tend to be worse inhibitors of trypsin than the corresponding ring unsubstituted compound. Preferred compounds (I) for use in a trypsin inhibitor role are therefore cinnamic acid ($X^1=X^2=X^3-X^4=X^5=H$, $R^1=R^2=H$, $R^3+R^4$=bond and $Y=CO_2H$) or an ester or salt derivative thereof and, at least in the case of bullfinches, cinnamamide ($X^1=X^2=X^3=X^4=X^5=H$, $R^1=R^2=H$, $R^3+R^4$=bond and $Y=CONH_2$).

As regards activity against chymotrypsin, when quail intestinal chymotrypsin was used in the test procedure, compounds (I) in which Y is $CO_2H$ or particularly CHO generally are effective inhibitors of chymotrypsin but, in this case, those in which Y is $CONH_2$ are less effective, compounds having a hydroxymethyl or cyano group Y being intermediate in their effect between those in which $Y=CONH_2$ and $CO_2H$. Compounds (I) having $R^1=R^2=R^3=R^4=H$ tend to be less effective than those having $R^1=R^2=H$ and $R^3+R^4$=bond but compounds in which $R^1=CH_3$, $R^2=H$ and $R^3+R^4$=bond can be as good or even slightly better than their equivalents in which $R^1$ is hydrogen. The major effect upon the inhibition of chymotrypsin has, however, been found to result upon substitution of the benzene ring of the compound (I) by substituents $X^2$, $X^3$ and $X^4$.

As a general rule, substitution at one of the 3, 4 and 5 positions of the benzene ring by a hydroxy or alkoxy group, for example a methoxy group, enhances the degree of inhibition, although this has been observed not to be the case for the compound 4-hydroxycinnamic acid ($X^1=X^2=X^4=X^5=H$, $X^3=OH$, $R^1=R^2=H$, $R^3+R^4$=bond, $Y=CO_2H$). Thus, the following compounds (I) have all been observed to be more effective than cinnamic acid at inhibiting chymotrypsin, the compounds being listed from 1 to 7 in ascending order of the level of inhibition observed (in each compound $R^1=R^2=H$, $R^3+R^4$=bond, $Y=CO_2H$).

(1) 3-Hydroxycinnamic acid ($X^1=X^3=X^4=X^5=H$, $X^2=OH$)
(2) 3-Methoxycinnamic acid ($X^1=X^3=X^4=X^5=H$, $X^2=OCH_3$)
(3) 3,5-Dimethoxycinnamic acid ($X^1=X^3=X^5=H$, $X^2=X^4=OCH_3$)
(4) 3,4-Dimethoxycinnamic acid ($X^1=X^4=X^5=H$, $X^2=X^3=OCH_3$)
(5% 3,4-Dihydroxycinnamic acid ($X^1=X^4=X^5=H$, $X^2=X^3=OH$)
(6) 3,4,5-Trimethoxycinnamic acid ($X^1=X^5=H$, $X^2=X^3=X^4=OCH_3$)
(7) 4-Hydroxy-3,5-dimethoxycinnamic acid ($X^1=X^5=H$, $X^2=X^4=OCH_3$, $X^3=OH$)

Preferred compounds for use in a chymotrypsin inhibitor role thus have two or three of $X^2$, $X^3$ and $X^4$, conveniently $X^3$ and one or both of $X^2$ and $X^4$, which are each separately hydroxy or alkoxy, particularly hydroxy or methoxy, $R^3+R^4$ conveniently being a bond 1 and $R^1$ and $R^2$ conveniently each being selected from hydrogen, methyl and ethyl, particularly from hydrogen and methyl, for example $R^1=R^2=H$ and $R^1=CH_3$, $R^2=H$, and Y conveniently being $CO_2H$ or an ester or salt derivative thereof or especially CHO. Particularly preferred compounds are the compounds (4), (5), (6) and (7) listed above and their analogues in which (a) $R^1=CH_3$, (b) Y=CHO and (c) $R^1=CH_3$ and Y=CHO.

It will be appreciated from the foregoing discussion that on the basis of enzyme activity such compounds showing a high level of inhibition of chymotrypsin may conveniently be used in conjunction with a compound, such as those described hereinbefore, showing a high level of inhibition of trypsin so that, for example, 4-hydroxy-3,5-dimethoxycinnamic acid and cinnamic acid used together would show a high level of inhibition of both enzymes. Alternatively a single compound (I)

may be employed showing an acceptable, if not high, level of inhibition of both enzymes, one candidate being 3,4-dihydroxy- cinnamic acid.

It will be appreciated that the present invention extends to those compounds falling within the general formula (I) which are novel per se.

Methods for synthesizing the compounds (I) of use in the present invention will be readily apparent to the man skilled in the art. Thus the compounds may be synthesized by procedures described in the art for those same compounds or analogues thereof, by modifications of the procedures, or by procedures described for related compounds or modifications thereof. In particular, cinnamic acid may conveniently be prepared by a Perkin reaction from benzaldehyde, for example using acetic acid and anhydrous sodium or potassium acetate, and ring substituted derivatives thereof may be prepared similarly from a substituted benzaldehyde. Compounds in which the carboxy group of cinnamic acid is modified may be prepared from the corresponding cinnamic acid with any necessary protection of ring substituents during the process. Thus for example cinnamamide may conveniently be prepared by the reaction of cinnamoyl chloride (which can be prepared from cinnamic acid by reaction with thionyl chloride, phosphorus trichloride or phosphorus pentachloride) with ammonia or by forming the ammonium salt of cinnamic acid by reaction with ammonia and then heating this to give cinnamamide, ring substituted derivatives being prepared by the use of a substituted cinnamic acid and N-substituted derivatives by the use of an appropriate amine in place of ammonia. The compound dihydrocinnamic acid in which $R^3$ and $R^4$ are each hydrogen may be prepared by the hydrogenation of the carbon-carbon double bond of cinnamic acid, for example in the presence of a nickel catalyst. Ring substituted derivatives may be prepared similarly with protection of the substituents where necessary, and compounds containing a group Y other than carboxy may either be prepared from the corresponding saturated compound in the same way with protection of the group Y where necessary or by modification of the carboxy group of the corresponding dihydrocinnamic acid.

Feeding trials have been conducted with both Japanese quail which have chymotrypsin as the major alkaline serine protease and feral pigeons which have trypsin as the major alkaline serine protease. Varying degrees of repellence have been observed but on the basis of a comparison of the proportions of treated and untreated food consumed in a two-choice test all of the compounds (I) had a deterrent effect on food consumption, this being most marked with 3,4,5-trimethoxycinnamic acid, 3,5-dimethoxycinnamic acid and cinnamamide in ascending order of effect. Cinnamamide was tested in both quail and pigeons when a deterrent effect on food consumption was noted in both species.

Accordingly, the compounds (I) are of interest in repelling a wide variety of birds irrespective of whether their main alkaline serine protease is chymotrypsin or trypsin, although the compounds are of particular interest in the case of some birds which present particular problems such as pigeons and bullfinches, and also starlings and sparrows, as well as geese, for example the Brent goose or the Canada goose (*Branta canadensis*), the red-winged blackbird (*Agelius phoeniceus*) and the brown-headed cowbird (*Molothrus ater*) particularly in the U.S.A., weaver birds, for example *Quelea quelea*, particularly in Africa, and the Indian house crow particularly in India and Africa.

A particular area of use of the compounds is in a horticultural context for the avoidance of damage to developing buds, particularly during the dormant season, especially fruit buds, for example of the top fruits apples, pears, plums, etc., to developing top fruit, particularly cherries, and to formed soft fruit prior to harvest, for example raspberries, strawberries, loganberries, blackberries, blackcurrants, gooseberries, etc. Other applications include protection of the seeds of growing crops, particularly sunflowers and oil seed rape. It will be appreciated, therefore, that the compounds (I) may be used for the protection of any plant material and that this may be in embryo, growing or harvested form, including the forms of seeds, seedlings, buds, leaves and other vegetative parts, and fruit. The compounds (I) are also of potential interest in any context where it is desirable to prevent bird damage, for example in the protection of structures and particularly electric cables from nibbling by birds.

The present invention thus includes a method for the treatment of a growing or harvested plant material, or any other substance which is exposed to birds, which comprises applying to that material or substance a compound of formula (I) as defined hereinbefore. The invention further extends to such plant material, for example fruit and seeds, or substance when so treated.

The compounds (I) may be formulated for application with various suitable types of diluent or carrier, particularly for agricultural/horticultural purposes, including aqueous formulations, oily formulations, etc. One suitable type of formulation involves the use of aqueous acetone as a diluent, especially with a higher proportion of water than acetone, such as 60–90% water:40–10% acetone (by volume), for example 80% water:20% acetone (by volume). However a variety of alternative diluents or carriers which are acceptable for application onto crops may conveniently be used to provide a solution, suspension, emulsion or powder containing the compound (I). In producing more complex forms of composition the aim is to enhance the activity of the compound through presenting it in a more effective physical form whilst avoiding any masking of the repellent effect by the mode of formulation. Of particular interest are slow release compositions which produce a more prolonged effect from a single application of the compound, the amount of the compound being maintained at an appropriate level through balancing the breakdown of the compound already released with the release of further amounts of the compound. Various conventional types of slow release formulation are suitable for this purpose but micro-encapsulation is of particular interest, for example in a polyurea capsule. In the case of compositions for treating harvested seeds solid carriers, for example one of various clays such as kaolin and bentonite, may conveniently be used to provide powder formulations, together with an emulsifying agent where appropriate.

Various other components may be included with the compounds (I) in a composition of use in the present invention. These include emulsifying agents for enhancing both the preparation of the composition and its application to the plant or other material. Suitable emulsifying agents are particularly the non-ionic surface active agents and especially those based on a polyether structure, for example polyoxyethylene stearate and nonylphenylpolyoxyethanol. Other types of additional component which may be considered for inclusion in the composition include various colouring agents, for example the commercially available materials Rhoplex AC-33, Trition AE and Acronal 4D (BASF), since birds are repelled by unfamiliar or aversive visual clues, agents which enhance adhesion of the composition to the material substance to which it is applied, for example Sky Blue and other commercially available food colourings, as well as insecticides, fungicides, etc., as appropriate. It will also be appreciated that the composition may contain more than one compound (I), for example one which is particularly effective in inhibiting chymotrypsin and another which is particularly effective in inhibiting trypsin, since this is often a more convenient approach than applying two such compounds separately.

Treatment will be applied at an appropriate time, for example either in advance or in response to bird attack. For the protection of fruit buds such treatment is commonly applied during the dormant season, i.e. the late autumn, winter and early spring, for example from November to February in the United Kingdom. The application of the composition containing the compounds (I) may conveniently be effected by standard means, and often by spraying, for example by the use of drum sprayers in orchards and may be repeated as necessary to maintain the desired level of control. Further general information concerning the formulation and use of avian repellents is provided by data on the use of existing repellents such as anthraquinone, thiram, aluminium ammonium sulphate, quassia extract and particularly methiocarb outside the United Kingdom.

The rate of application of the compounds will depend both upon the particular compound (I) which is being used and upon the nature and location of the substance being treated. However, by way of guidance it may be stated that for the treatment of growing crops an application rate of 0.1 to 100, particularly 1 to 10 kilograms per hectare, of the compound (I) is often appropriate, the aim being to use the minimum effective quantity which may, for example, be 5 kilograms per hectare or a lesser amount as indicated. For the treatment of harvested crops, for example seeds, an application rate of 0.01 to 1, particularly 0.05 to 0.5% w/w, of the compound (I) to treated material is often appropriate. Once again, the aim is to use the minimum effective quantity which may, for example, be 0.1% w/w or a lesser amount as indicated.

BRIEF DESCRIPTION OF THE DRAWINGS

The invention is illustrated by the following Examples with reference to the accompanying drawings, in which.

Figure 1A:
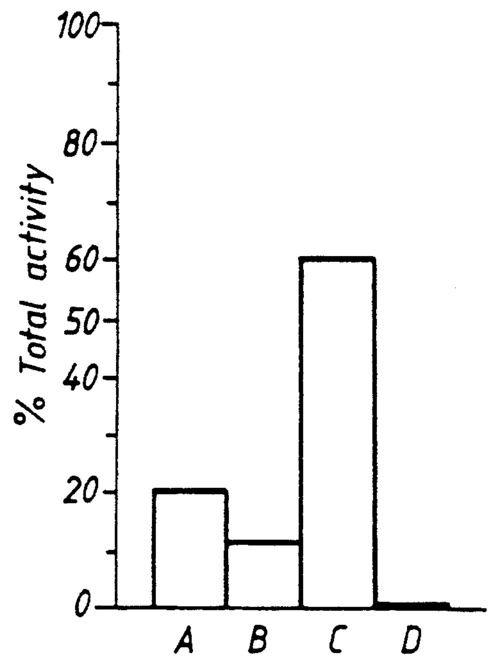
FIGS. 1*a*–1*c* show the results of the determinations of acid and alkaline protease activity in the gizzard and small intestine for the Japanese quail (FIG. 1*a*), the bullfinch (FIG. 1*b*) and the pigeon (FIG. 1*c*)

EXAMPLES (The compounds of formula (I) used herein were predominantly of the trans isomeric form.)

EXAMPLE 1

Studies with Avian Proteases

(A) Preparation of Protease Extracts

The birds (five week old female Japanese quail, wild, trapped bullfinches or feral pigeons) were sacrificed and the small intestine and gizzard were removed and immersed in liquid nitrogen for 5 minutes. The frozen gizzard and small intestine tissues were then lyophilised separately for 24 hours, ground to a fine powder in a hammer mill and stored, dessicated at −20° C., until required for analysis.

Dried avian gut tissue powder (500 mg) was extracted for 30 minutes in the appropriate buffer [acid protease assay: 10 mM HCl (10 ml)/alkaline protease assay: 100 mM Tris-HCl (Tris is an abbreviation for 2-amino-2-hydroxymethylpropane 1,3-diol) buffer of pH 7.0 (10 ml)] at ambient temperature. The extract was centrifuged at 22,000×g for 30 minutes at 4° C. and the resultant supernatant removed for subsequent assays.

(B) Determination of Protease Activity (1) Acid protease activity was determined by the method of Rick and Fritsh, Methods of Enzymatic Digestion, 1974, 2nd edition, page 1046 (edited by Bergmeyer, Academic Press Inc., London), using a haemoglobin substrate. The reaction was carried out in 4 ml plastic disposable test tubes containing the haemoglobin substrate [bovine haemoglobin lyophilised powder, 200 mg/ml in 10 mM HCl (i.e. 10 mM aqueous hydrochloric acid) (1 ml)] and 10 mM HCl (400 μl). The reaction was started by the addition of gut extract (200 μl) and stopped after 10 minutes by the addition of 5% (W/v) trichloroacetic acid (2 ml). The tubes were mixed and centrifuged at 4000×g for 20 minutes. An aliquot of the resultant supernatant (1 ml) was added to 0.5M NaOH (2 ml) in a plastic cuvette ($1\times1\times4$ cm$^3$). Folin-Ciocalteu reagent diluted 1:3 v/v with distilled water (0.6 ml of diluted reagent) was added and the absorbance at 691 nm determined against a reagent blank after 9 minutes. All determinations were carried out in triplicate.

(2) Alkaline protease activity was determined using a denatured haemoglobin substrate. This was produced by mixing haemoglobin (0.5 mg) with distilled water (10 ml), urea (9 g) and 1M NaOH (2 ml) and leaving for 1 hour. Calcium chloride (5% w/v, 1.1 ml) and boric acid solution (1M+7 mM NaCl, 2.5 ml) were then added, the pH adjusted to 7.5 with HCl, the volume made up to 25 ml with water and the solution centrifuged at 4,000×g for 20 minutes. The assay was carried out using this substrate as described for the assay of acid protease activity with the exception that 100 mM Tris HCl buffer of pH 7.5 was used instead of 10 mM HCl as the reaction medium.

Figure 1B:
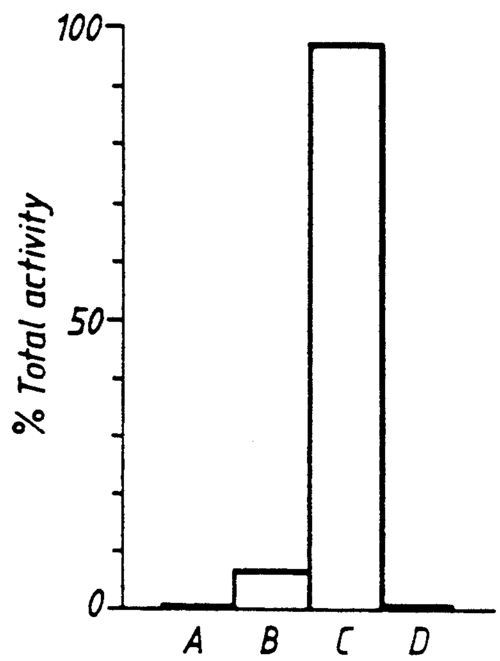
Figure 1C:
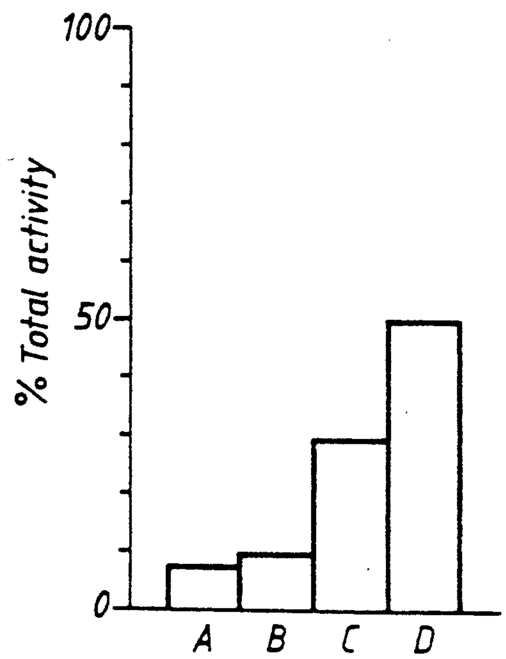

The results of the determination of acid and alkaline protease activity in the gizzard and small intestine are shown in FIG. 1*a* for the Japanese quail, in FIG. 1*b* for the bullfinch, and in FIG. 1*c* for the pigeon. In each FIG., A relates to the alkaline gizzard, B to the acid gizzard, C to the alkaline intestine and D to the acid intestine, the results being expressed as percentages of the total protease activity observed. It will be seen from FIG. 1*a* that the predominant protease activity found in the quail alimentary canal is of an alkaline serine protease type in both the gizzard and the small intestine. Since the pH of the avian gizzard is about 2.0 any alkaline protease activity in this tissue would be unlikely to manifest itself and, conversely, any acid proteases in the intestine, which is about pH 7.0, would also be inactive. In the case of the bullfinch, it will be seen from FIG. 1*b* that the predominant protease activity found in the alimentary canal is again of an alkaline serine protease type but that in the gizzard it is of an acid serine protease type. In the case of the pigeon, it will be seen from FIG. 1*c* that the alimentary canal has substantial acid and alkaline serine protease activity but the former will be inactive at the pH of about 7.0 and, in the grizzard, the slightly higher acid serine protease activity will be that prevailing as the alkaline serine protease activity will not be evident at the pH of about 2.0.

(C) Determination of chymotrypsin/trypsin activity in intestine (1) Partial Purification of the small intestine protease Dried avian intestine powder (500 mg) was extracted for 30 minutes in 1 mM HCl (5 ml). The extract was centrifuged at 22,000×g for 30 minutes at 4° C. The resultant supernatant was applied to a column of Sephadex G-50, medium grade (360 mm×15 mm) and eluted with 0.5 mM HCl at 0.7 ml/min. Fractions (3.5 ml) were collected and tested for the presence of protein by determining their absorbance at 280 nm. The proteinaceous fractions were bulked and concentrated by passing them through an ultrafiltration unit (YM 30 filter). The concentrate was collected and kept at 4° C. throughout its use.

(2) Determination with specific substrates

N-Acetyl-L-tyrosine ethyl ester (ATEE) assay (chymotrypin)

The substrate was prepared by dissolving ATEE (10 mg) in Tris-HCl buffer of pH 7.5 containing 30% (v/v) of methanol (25 ml). The quail intestine protease activity was partially purified as described above prior to testing for chymotrypsin activity. The reaction was carried out in a quartz cuvette ($1\times0.25\times1$ cm$^3$) containing substrate (1 ml) and 100 mM Tris-HCl buffer (200 μl). The reaction was started by the addition of the partially purified intestine protease (200 μl) and followed by the decrease in absorbance at 237 nm over a 5 minute period. All determinations were carried out in triplicate against a reagent blank.

(N-Benzoyl-L-arginine ethyl ester (BAEE) assay (trypsin—bullfinch)

The substrate was prepared by dissolving BAEE (10 mg) in a mixture of 50 mM Tris-HCl buffer of pH 7.5 (24 ml) and 5% (w/v) calcium chloride solution (1 ml). The bullfinch intestine protease activity was partially purified as described above prior to testing for trypsin activity. The reaction was carried out in a quartz cuvette ($1\times0.25\times1$ cm$^3$) containing substrate (1 ml) and 50 mM Tris-HCl buffer (200 μl). The reaction was started by the addition of the partially purified intestine protease (200 μl) and followed by the decrease in absorbance at 253 nm over a 7 minute period. All determinations were carried out in triplicate against a reagent blank.

N-p-Toluenesulfonyl-L-arginine methyl ester (TAME) assay (trypsin-pigeon)

The substrate was prepared by dissolving TAME (19 mg) in a mixture of 100 mM Tris-HCl buffer of pH 7.5 (50 ml) and 5% (w/v) calcium chloride solution (2 ml). The pigeon intestine protease was partially purified as described above prior to testing for trypsin activity. The reaction was carried out in a quartz cuvette ($1\times0.25\times1$ cm$^3$) containing substrate (3 ml) and 100 mM Tris-HCl buffer pH 7.5 (100 μl). The reaction was started by the addition of the partially purified intestine protease (100 μ) and followed by the decrease in absorbance at 247 nm over a 5 minute period.

Figure 2A:
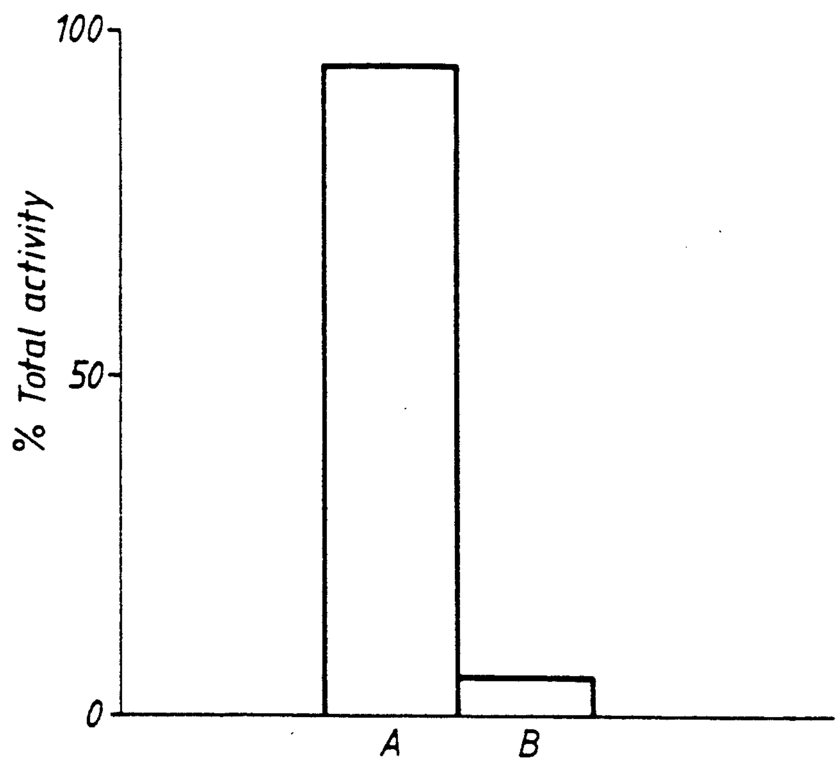
FIGS. 2*a*–2*b* show the results of the determinations of chymotrypsin and trypsin activity in the small intestine for the Japanese quail (FIG. 2*a*) and the bullfinch (FIG. 2*b*)
Figure 2B:
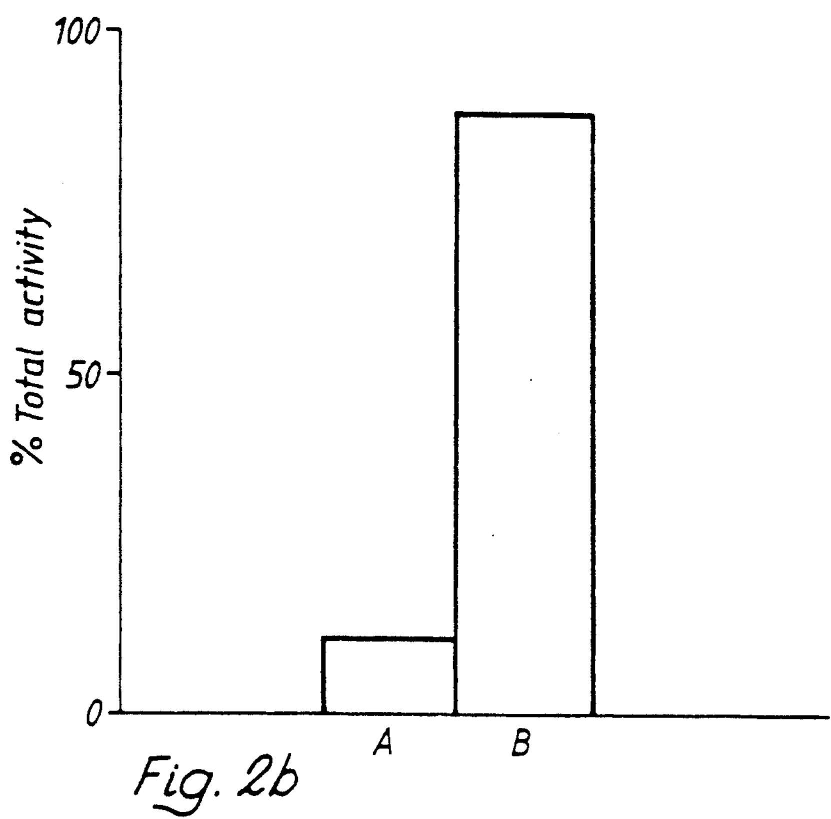

The results of the determinations of chymotrypsin and trypsin activity in the small intestine are shown in FIG. 2*a* for the Japanese quail and in FIG. 2*b* for the bullfinch. In the Figures, A relates to chymotrypsin (ATEE assay) and B to trypsin (BAEE assay). It will be seen that chymotrypsin is responsible for most of the detectable quail intestinal protease activity but that trypsin is responsible for most of the detectable bullfinch intestinal protease activity. In the case of the pigeon, chymotrypsin was substantially absent to that essentially all of the intestinal protease activity was due to trypsin.

(D) Inhibition of Chymotrypsin/trypsin Activity

The ATEE, BAEE and TAME assay procedures were carried out as described above but adding to the substrate one of a series of compounds (I) or one of an alternative group of compounds to provide a comparison with the compounds (I), the compound either (a) in the ATEE and BAEE assays being made up to a concentration of $1\times10^{-5}$M by addition in 100 mM Tris-HCl buffer of pH 7.5 (100 μl) which replaced the 200 μl of this buffer mixed in the cuvette with the substrate, or (b) in the TAME assay being made up to a concentration of 60 μg/ml by addition at 2 mg/ml in 100 mM Tris-HCl buffer of pH 7.5 (100 μl) which is added to the 100 μl of this buffer already present. In both the chymotrypsin and the trypsin assays a control was however carried out using the 200 μl of buffer containing no added compound.

The results obtained are shown in Table 1 for the quail chymotrypsin and bullfinch trypsin, and in Table 1 (A) for the pigeon trypsin, the figures being given as percentage inhibition of control activity, together with a standard deviation (n=3) (a dash indicates that the compound in question was not tested with bullfinch trypsin preparation which was available only in limited quantities).

TABLE 1

Inhibition of quail chymotrypsin/bullfinch trypsin activity

| | Inhibition of Activity | |
|---|---|---|
| Compound | Chymotrypsin | Trypsin |
| Cinnamic Acid | 32 ± 3 | 85 ± 2 |
| Cinnamaldehyde | 57 ± 4 | — |
| Cinnamamide | 5 ± 1 | 64 ± 2 |
| α-Methylcinnamic acid | 36 ± 3 | — |
| α-Methylcinnamaldehyde | 17 ± 5 | — |
| Cinnamonitrile | 23 ± 1 | — |
| Cinnamyl alcohol | 20 ± 6 | — |
| Hydrocinnamic acid | 19 ± 3 | — |
| 4-Hydroxycinnamic acid | 12 ± 1 | — |
| 3-Hydroxycinnamic acid | 43 ± 2 | — |
| 3-Methoxycinnamic acid | 56 ± 4 | — |
| 3,4-Dihydroxycinnamic acid | 85 ± 2 | 43 ± 3 |
| 3,4-Dimethoxycinnamic acid | 83 ± 3 | — |
| 3,5-Dimethoxycinnamic acid | 63 ± 1 | — |
| 3,4,5-Trimethoxycinnamic acid | 88 ± 2 | 36 ± 1 |
| 4-Hydroxy-3,5-dimethoxy-cinnamic acid | 94 ± 2 | 22 ± 2 |
| Phenylacetic acid | 13 ± 2 | — |
| Benzoic acid | 14 ± 1 | — |
| 4-Hydroxy-3,5-dimethoxy- | 2 ± 2 | — |

TABLE 1-continued

| Inhibition of quail chymotrypsin/bullfinch trypsin activity | | |
|---|---|---|
| | Inhibition of Activity | |
| Compound | Chymotrypsin | Trypsin |
| benzoic acid | | |

TABLE 1(A)

| Inhibition of pigeon trypsin activity | |
|---|---|
| Compound | Inhibition of Activity |
| Cinnamic Acid | 93 ± 3 |
| Cinnamamide | 0 |
| 3,4-Dihydroxycinnamic acid | 22 ± 1 |
| 3,4-Dimethoxycinnamic acid | 16 ± 1 |
| 3,5-Dimethoxycinnamic acid | 14 ± 1 |
| 4-Hydroxy-3-methoxycinnamic acid | 16 ± 4 |
| 3,4,5-Trimethoxycinnamic acid | 0 |
| 4-Hydroxy-3,5-dimethoxy-cinnamic acid | 16 ± 4 |
| 3-(3',4'-Dihydroxycinnamoyl)-quinic acid | 3 ± 1 |
| Turkey egg white trypsin inhibitor | 64 ± 3 |
| Dimethylanthranilate | 9 ± 2 |

EXAMPLE 2

Feeding Trails with Japanese Quail (A) Six week old female Japanese quail were preconditioned by weighing them seven days before the start of the feeding trial. Five quail were placed in each of four cages and each cage was provided with a different diet, these being (a) a control diet of standard turkey starter crumbs (TSC), (b) TSC treated with 5,000 ppm cinnamamide, (c) TSC treated with 5,000 ppm 4-hydroxy-3,5-dimethoxycinnamic acid, and (d) TSC treated with 2,500 ppm cinnamamide+2,500 ppm 4-hydroxy-3,5-dimethoxycinnamic acid. The treated TSC was prepared in each case by dissolving/suspending the compound or compounds in diethyl ether (1500 ml) and mixing this with TSC (2000 g) at 0.25% or 0.5% w/w concentration compound/TSC in an industrial food mixer for 1 hour to evaporate off the diethyl ether and produce a homogeneous mixture. The control was prepared by mixing TSC (2000 g) with diethyl ether for 1 hour in an industrial food mixer. The amount of each diet consumed and the weight gain of the birds was recorded on a daily basis for a period of 14 days. The trail was carried out in duplicate.

The results of the trail are presented in Table 2, together with the standard deviation. It will be seen that diets (b) and (d) produced a decreased increase in body weight as compared with the control diet (a). It should be appreciated that increased consumption, which apparently occurs with diets (c) and (d), can be the result of a compensation against the occurrence of the enzyme inhibitory effect and a consequent reduction in value of the food consumed.

(B) In a variation of the treatment described in (A) four quail were placed in each of four cages and each cage was offered a choice between a control diet of TSC and TSC treated with one of (a) 5,000 ppm cinnamamide, (b) 2,500 ppm cinnamamide, (c) 1,000 ppm cinnamamide, and (d) 2,500 ppm cinnamamide+2,500 ppm 4-hydroxy-3,5-dimethoxycinnamic acid. The various diets were prepared as described under (A).

The results of the trail are presented in Table 3, together with the standard deviation. It will be seen that in each case the birds consume less treated than untreated food and that although the weight gain was the least for the birds offered the control+5,000 ppm cinnamamide diets, it was the 2,500 ppm cinnamamide+2,500 ppm 4-hydroxy-3,5-dimethoxycinnamic acid diet which was least consumed.

TABLE 2

| No choice feeding trials | | | |
|---|---|---|---|
| Diet | Concentration of additive (ppm) | Increase in body weight (g/bird/day) | Average food eaten (g/bird/day) |
| Control | — | 0.66 ± 0.10 | 19 ± 0.3 |
| Cinnamide | 5,000 | 0.14 ± 0.04 | 17 ± 0.3 |
| 4-Hydroxy-3,5-dimethoxycinnamic acid | 5,000 | 0.89 ± 0.10 | 21 ± 0.3 |
| Cinnamamide + 4-hydroxy-3,5-dimethoxycinnamic acid | 2,500 each | 0.36 ± 0.10 | 21 ± 0.2 |

TABLE 3

| Feeding trials with choice | | | |
|---|---|---|---|
| Diet | Concentration of additive (ppm) | Increase in body weight (g/bird/day) | Average food eaten (g/bird/day) |
| Control | — | 0.66 ± 0.10 | 12 ± 0.5 |
| Cinnamamide | 5,000 | | 4 ± 0.2 |
| Control | — | 1.34 ± 0.20 | 15 ± 0.4 |
| Cinnamamide | 2,500 | | 5 ± 0.4 |
| Control | — | 1.29 ± 0.10 | 11 ± 0.2 |
| Cinnamamioe | 1,000 | | 6 ± 0.2 |
| Control | — | 1.35 ± 0.2 | 15 ± 0.3 |
| Cinnamamide + 4-hydroxy-3,5-dimethoxycinnamic acid | 2,500 each | | 3 ± 0.2 |
| 6 ± 0.2 | | | |

EXAMPLE 3

Feeding Trails with Feral Pigeons

Feral pigeons were transferred from a communal outdoor aviary to individual cages and maintained on a 10 hour light-14 hour dark cycle. Birds were gradually weaned away from their normal diet of maize, wheat and maple peas to a standard laboratory diet of turkey starter pellets. All birds lost weight during the first few days as they adjusted to their new conditions. Most began to regain weight after 3 or 4 days. Some birds could not adapt, continued to lose weight and were removed from the experiment. After about two to three weeks the bird weights were more or less stable and the trials were commenced.

The birds were tested with a range of compounds (I) and also with sucrose octaacetate and dimethyl anthranilate which are known to be offensive to birds. The compounds for testing were each dissolved in an 80/20 v/v acetone/water mixture and sprayed onto turkey starter pellets to give a 0.5% w/w compound/pellet concentration. The pellets were oven dried and then left to absorb atmospheric moisture. The control food was sprayed with the same volume of acetone/water mixture.

A group of 35 feral pigeons was caged individually for the trials which used eight compounds of formula (I) together with sucrose octaacetate and dimethyl anthranilate, both of which are substances which are known to be avian repellents. Each bird was subjected to treatment with each compound in a random order subject to the limitation of a latin square design. Each treatment was presented to the birds in no-choice and two-choice conditions. The no-choice phase lasted 3 days, during which a bird was presented with a single bowl containing 120 g of treated food. Each bird was weighed before and after the no-choice phase, as was the amount of food remaining. There immediately followed a two-choice phase in which the birds could choose between food treated with a given chemical and a bowl containing otherwise identical pellets without the chemical (the control treatment utilizing two bowls of acetone/water treated pellets, one of which was arbitrarily selected as the control). The two-choice phase lasted four days during which food consumption was monitored daily. The position of the food bowls was alternated each day in order to overcome the confusing of food preference with position preference and ample water and grit were supplied throughout the trail.

The data obtained in the three day no-choice test is presented in Table 4 for both mean consumption of treated food in grams during the test and for mean weight difference in grams after the test as compared with before the test, the standard deviation being given after each figure. It will be seen that the most marked reduction in consumption as compared with the control and in mean weight difference occurs with 3,5-dimethoxycinnamic acid and most particularly with cinnamamide, the difference being greater than that observed with sucrose octaacetate or dimethyl anthranilate.

TABLE 4

| Compound | No-choice test | |
|---|---|---|
| | Mean consumption grams | Mean weight difference grams |
| Control | 59.8 ± 2.4 | 1.7 ± 0.8 |
| Cinnamic acid | 60.4 ± 3.1 | 2.4 ± 1.1 |
| Cinnamamide | 22.3 ± 2.7 | −16.2 ± 1.3 |
| 3,4-Dihydroxycinnamic acid | 63.3 ± 3.0 | 2.3 ± 1.1 |
| 3,4-Dimethoxycinnamic acid | 55.3 ± 2.3 | −1.1 ± 0.9 |
| 3,5-Dimethoxycinnamic acid | 33.1 ± 1.5 | −12.9 ± 1.2 |
| 4-Hydroxy-3-methoxy-cinnamic acid | 54.5 ± 2.9 | −0.2 ± 1.1 |
| 3,4,5-Trimethoxy-cinnamic acid | 53.0 ± 2.1 | −1.5 ± 0.9 |
| 4-Hydroxy-3,5-dimethoxycinnamic acid | 60.2 ± 3.3 | 2.3 ± 0.9 |
| Sucrose octaacetate | 54.0 ± 2.6 | 2.3 ± 0.9 |
| Dimethyl anthranilate | 45.9 ± 2.9 | −4.8 ± 2.0 |

The data obtained in the four day two-choice test is presented in Table 5 for mean consumption of treated food. It can be seen that in agreement with the results of the no-choice tests it is the 3,5-dimethoxycinnamic acid and particularly the cinnamamide treated food which is consumed least and particularly at a lower level than dimethyl anthranilate.

TABLE 5

| | Compound | Two-choice test<br>Mean consumption of treated food grams |
|---|---|---|
| (1) | Control | 42.3 ± 2.8 |
| (2) | Cinnamic acid | 25.2 ± 2.9 |
| (3) | Cinnamamide | 6.0 ± 1.5 |
| (4) | 3,4-Dihydroxycinnamic acid | 31.1 ± 3.4 |
| (5) | 3,4-Dimethoxycinnamic acid | 27.1 ± 2.8 |
| (6) | 3,5-Dimethoxycinnamic acid | 12.1 ± 1.7 |
| (7) | 4-Hydroxy-3-methoxy-cinnamic acid | 22.7 ± 2.4 |
| (8) | 3,4,5-Trimethoxycinnamic acid | 19.8 ± 2.7 |
| (9) | 4-Hydroxy-3,5-dimethoxy-cinnamic acid | 29.2 ± 2.8 |
| (10) | Sucrose octaacetate | 28.6 ± 2.4 |
| (11) | Dimethyl anthranilate | 18.2 ± 2.4 |

Figure 3:
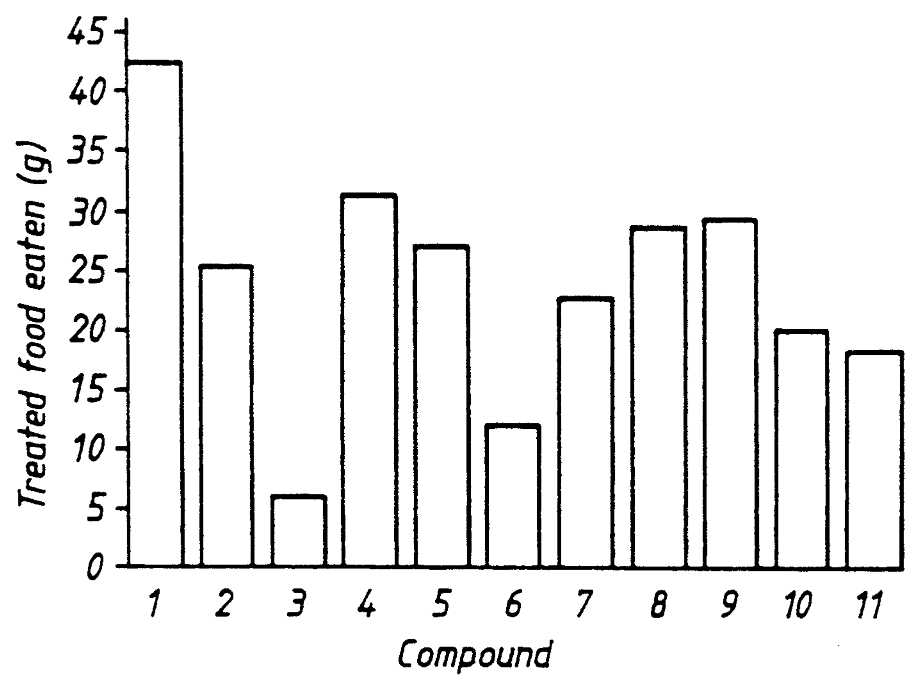
FIG. 3 is a histogram presenting the results of Table 5 appearing hereinbelow.

The data is also presented as a histogram in FIG. 3, the compounds being referenced as in Table 5, from which it will be seen that for all of the compounds (I) treatment of food with the compound has a repellent effect as shown by the decreased consumption of food as compared with the acetone/water-treated food of the control experiment.

EXAMPLE 4

Field Trial in Pear Orchards

Cinnamic acid and 3,4-dihydroxycinnamic acid were tested in the field for their ability to deter bullfinches from feeding on developing buds on pear trees. Levels of damage were monitored in two commercial orchards from early February to April by regularly scoring the proportions of buds pecked by bullfinches in a standard sample of 50 buds on each tree. When damage had reached a moderate level, 20 trees in each orchard were chosen for experimental spraying, these trees being in a band several meters from the edge of the orchard where approximately 10–20% of the buds were affected. A part of each tree containing about 250 buds was sprayed, and subsequent damage was counted and compared to damage on (a) another part of the same tree and (b) and adjacent, unsprayed tree. In the first orchard cinnamic acid was used (25 g in an 80:20 v/v acetone:water mixture), being applied from a knapsack sprayer, and in the second orchard 3,4-dihydroxy-cinnamic acid was applied at a similar level and by a similar method. For both compounds a second spray was applied one week later.

The results are summarized in Table 6 from which it will be seen that in the first orchard there was significantly less damage on the parts of trees that were sprayed with cinnamic acid that there was on other branches of the same trees, this result being observed after both sprays. In the second orchard a similar pattern was evident, but this was at a lesser level of significance and it was stronger when the sprayed branches were compared to adjacent trees rather than to unsprayed branches on the same tree.

A fall off was observed with time in the birds' avoidance of sprayed branches due to a loss of residues of the compounds from the buds, this being more marked with the 3,4-dihydroxycinnamic acid than with the cinnamic acid (the residues as a percentage of the initial level having fallen to 8% for 3,4-dihydroxycinnamic acid after 8 days, whilst for cinnamic acid they were 41% after 8 days and 3% after 51 days). The trials do, however, indicate the potential of these compounds in avian control.

TABLE 6

Field trial

| Compound applied | Number of sprays | Days after last spray | Number of trees out of 20 having less damage and significance(1) than unsprayed branches | than adjacent trees |
|---|---|---|---|---|
| cinnamic acid | 1 | 1 | 16/20 ** | 11/20 NS |
| " | 1 | 4 | 11/20 NS | 9/20 NS |
| " | 2 | 1 | 17/20 *** | 11/20 NS |
| " | 2 | 4 | 14/20 NS | 9/20 NS |
| 3,4-dihydroxy-cinnamic acid | 1 | 1 | 14/20 NS | 14/20 NS |
| 3,4-dihydroxy-cinnamic acid | 1 | 4 | 13/20 NS | 11/20 NS |
| 3,4-dihydroxy-cinnamic acid | 2 | 1 | 13/20 NS | 15/20 * |
| 3,4-dihydroxy-cinnamic acid | 2 | 4 | 10/20 NS | 10/20 NS |

(1)The significance was tested by one-tailed binomial tests, the level of significance being in the order * >  > * > NS and it is believed that the relatively low level of significance observed was in part due to the small number of trees used.

We claim:

1. A method of treating a plant material which is an embryo, growing or harvested crop to confer avian repellency, which method comprises applying to said plant material in an amount sufficient to confer avian repellency (a) a compound of formula (I)

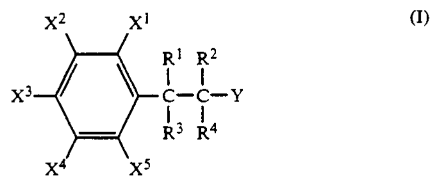

wherein $X^1$ and $X^5$ are each separately selected from hydrogen and $C_{1-4}$ alkyl groups; $X^2$, $X^3$ and $X^4$ are each separately selected from hydrogen and $C_{1-4}$ alkyl, hydroxy, $C_{1-4}$ alkoxy and phenoxy groups; $R^1$ and $R^2$ are each separately selected from hydrogen and $C_{1-4}$ alkyl groups; $R^3$ and $R^4$ are each hydrogen or together constitute the second bond of a carbon—carbon double bond joining —$CR^1R^3$— and —$CR^2R^4$—; and Y is carbamoyl or carbamoyl N-substituted by one or two of the same or different $C_{1-4}$ groups and/or (b) a compound being 3,5-dimethoxycinnamic acid or a carboxylic ester or carboxylate salt thereof.

2. A method according to claim 1, in which the compound used is a compound of formula (I)

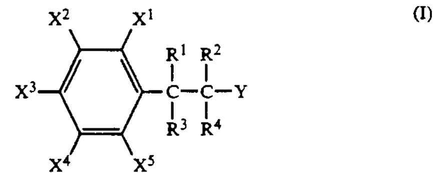

wherein $X^1$ and $X^5$ are each separately selected from hydrogen and $C_{1-4}$ alkyl, halogeno and halogeno-substituted $C_{1-4}$ alkyl groups; $X^2$, $X^3$ and $X^4$ are each separately selected from hydrogen and $C_{1-4}$ alkyl, hydroxy, $C_{1-4}$ alkoxy and phenoxy groups, $R^1$ and $R^2$ are each separately selected from hydrogen and $C_{1-4}$ alkyl groups; $R^3$ and $R^4$ are each hydrogen or together constitute the second bond of a carbon-carbon double bond joining —$CR^1R^3$—and —$CR^2R^4$—; and Y is carbamoyl or carbamoyl N-substituted by one or two of the same or different $C_{1-4}$ alkyl groups.

3. A method according to claim 1, in which the compound used is 3,5-dimethoxycinnamic acid or a carboxylic ester or carboxylate salt thereof.

4. A method according to claim 3, in which the compound used is 3,5-dimethoxycinnamic acid.

5. A method according to claim 1, in which $X^1$ and $X^5$ are each separately selected from hydrogen and $C_{1-4}$ alkyl.

6. A method according to claim 1, in which $X^2$, $X^3$ and $X^4$ are each separately selected from hydrogen, $C_{1-4}$ alkyl and $C_{1-4}$ alkoxy groups.

7. A method according to claim 1, in which $R^1$ and $R^2$ are each hydrogen and $R^3$ and $R^4$ together constitute the second bond of a carbon-carbon double bond.

8. A method according to claim 1, in which Y is carbamoyl.

9. A method of treating a plant material which is an embryo, growing or harvested crop to confer avian repellency, which method comprises applying to said plant material in an amount sufficient to confer avian repellency a compound of formula (II)

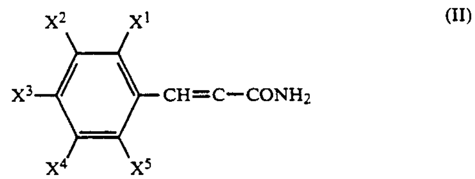

wherein $X^1$ and $X^5$ are separately selected from hydrogen and $C_{1-4}$ alkyl groups, and $X^2$, $X^3$ and $X^4$ are each separately selected from hydrogen and $C_{1-4}$ alkyl, hydroxy, $C_{1-4}$ alkoxy groups.

10. A method according to claim 9, in which $X^1$ and $X^5$ are each hydrogen.

11. A method according to claim 9, in which $X^2$ and $X^4$ are each separately a $C_{1-4}$ alkoxy group.

12. A method according to claim 9, in which $X^2$ and $X^4$ are each methoxy.

13. A method according to claim 9, in which the compound is 3,5-dimethoxycinnamamide.

14. A method according to claim 9, in which the compound is cinnamamide.

15. A method of treating a plant material which is an embryo, growing or harvested crop to confer avian repellency, which method comprises applying to said plant material in an amount sufficient to confer avian repellency two or more of (a) 3,5-dimethoxycinnamic acid and its esters and salts,
(b) 3,5-dimethoxycinnamamide,
(c) 3,4,5-trimethoxycinnamamide, and
(d) cinnamamide.

16. A method according to claim 1, in which the compound is used together with a coloring agent.

17. A method according to claim 1, in which the birds are pigeons, bullfinches, starlings or sparrows.

18. A method according to claim 17, in which the birds are pigeons.

19. A method according to claim 1, wherein said plant material which is treated is seeds.

20. A method according to claim 1, wherein said plant material which is treated is fruit.

* * * * *

UNITED STATES PATENT AND TRADEMARK OFFICE
CERTIFICATE OF CORRECTION

PATENT NO. : 5,196,451

DATED : March 23, 1993

INVENTOR(S) : GREIG-SMITH et al

It is certified that error appears in the above-identified patent and that said Letters Patent is hereby corrected as shown below:

Column 15 lines 61-62, delete ", halogeno and halogeno-substituted $C_{1-4}$ alkyl groups"

Column 16 lines 9-10, delete "separately selected from hydrogen and $C_{1-4}$ alkyl" and replace by --hydrogen--

Column 16 line 25, delete the formula (II) and replace by the following formula:

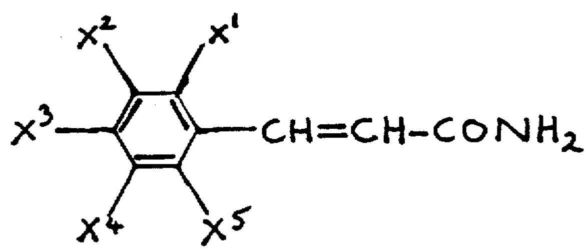

Column 16 line 36, delete "droxy, $C_{1-4}$ alkoxy groups." and and replace by --droxy and $C_{1-4}$ alkoxy groups.--

Signed and Sealed this

Twenty-second Day of March, 1994

Attest:

BRUCE LEHMAN

Attesting Officer

Commissioner of Patents and Trademarks